United States Patent

Ellis et al.

[11] 4,024,255
[45] May 17, 1977

[54] TETRAZOLE CONTAINING NAPHTHYRIDINE-3-CARBOXAMIDES

[75] Inventors: Gwynn Pennant Ellis, Cardiff, Wales; Ian Collins, London, England; David Martin Waters, London, England; David Edmund Bays, London, England

[73] Assignee: Allen & Hanburys Limited, London, England

[22] Filed: Sept. 25, 1975

[21] Appl. No.: 616,880

Related U.S. Application Data

[62] Division of Ser. No. 455,072, March 27, 1974, Pat. No. 3,943,141.

[30] Foreign Application Priority Data

Apr. 5, 1973  United Kingdom ............ 16278/73

[52] U.S. Cl. .................. 424/248.54; 260/247.2 A; 260/293.59; 260/268 BC; 260/295.5 B; 424/45; 424/46; 424/250; 424/256

[51] Int. Cl.² ............. C07D 471/04; A61K 31/535

[58] Field of Search .......... 260/247.2, 268, 293.69, 260/295.5, 247.2 A, 268 BC, 293.59, 295.5 B; 424/248, 250, 256, 266, 248.54

[56] References Cited

UNITED STATES PATENTS

| | | | |
|---|---|---|---|
| 3,149,104 | 9/1964 | Lesher et al. | 260/295.5 B |
| 3,590,036 | 6/1971 | Lesher et al. | 260/295.5 B |
| 3,644,353 | 2/1972 | Lunts et al. | 260/559 S |
| 3,803,230 | 4/1974 | Lunts et al. | 260/559 S |

OTHER PUBLICATIONS

Morrison et al., Organic Chemistry, pp. 486–487 (1959).

Primary Examiner—John M. Ford
Assistant Examiner—R. W. Ramsuer
Attorney, Agent, or Firm—Bacon & Thomas

[57] ABSTRACT

Compounds of the general formulae I and II and pharmaceutically acceptable salts thereof:

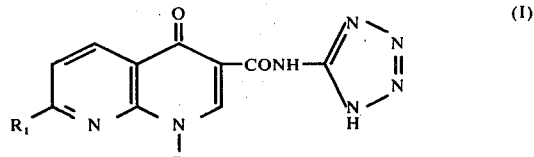

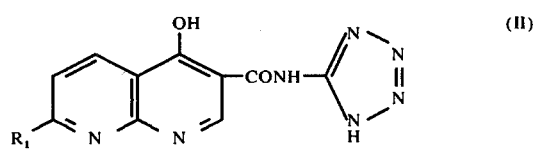

in which:

$R_1$ represents a hydrogen atom, a halogen atom, an alkenyl or alkyl group; or a group $OR_3$ or $NR_3R_4$ where $R_3$ and $R_4$ which may be the same or different and may represent a hydrogen atom, or an alkenyl group, or an alkyl group which alkyl group may optionally be substituted by one or more hydroxy, alkoxy, acyloxy, aryl, amino, alkylamino, dialkylamino, diaralkylamino or alkylaralkylamino groups; or $R_3$ and $R_4$ together with the nitrogen atom form a 5 or 6 membered heterocyclic ring that may optionally contain other hetero atoms.

$R_2$ has the same meanings as $R_3$.

The compounds have utility for the treatment of conditions in which combination of an antigen with a reaginic antibody is primarily responsible.

7 Claims, No Drawings

TETRAZOLE CONTAINING NAPHTHYRIDINE-3-CARBOXAMIDES

This is a division of application Ser. No. 455,072, filed Mar. 27, 1974 now U.S. Pat. No. 3,943,141.

This invention relates to certain novel naphthyridine derivatives which have been found to have a useful profile of pharmacological activity. It also relates to a process for the production thereof, to pharmaceutical compositions containing them and to their use in therapy.

The invention provides compounds of the general formula (I) below and (when $R_2$ = H) tautomers thereof of formula (II) and pharmaceutically acceptable salts thereof.

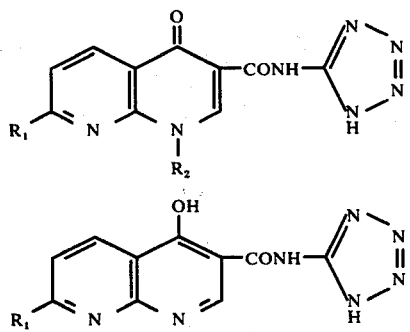

in which
$R_1$ represents a hydrogen atom, a halogen atom, an alkenyl or alkyl group; or a group $OR_3$ or $NR_3R_4$ and $R_3$ and $R_4$ which may be the same or different and may represent a hydrogen atom, or an alkenyl group, or an alkyl group which alkyl group may optionally be substituted by one or more hydroxy, alkoxy, acyloxy, aryl, amino, alkylamino, dialkylamino, diaralkylamino or alkylaralkylamino groups; or $R_3$ and $R_4$ together with the nitrogen atom form a 5 or 6 membered heterocyclic ring that may optionally contain other hetero atoms.

$R_2$ has the same meanings as $R_3$.

The term "alkyl" when used above to define a single group or part of a group refers to a straight or branched chain alkyl group containing from 1 to 6 carbon atoms, and preferably 1 to 4 carbon atoms and the term "alkenyl" refers to a straight or branched chain alkenyl group containing from 2 to 6 carbon atoms, and preferably from 3–5 carbon atoms.

The term "aryl" preferably refers to a phenyl group and the term "acyloxy" preferably refers to an alkanoyloxy group containing 1 to 6 carbon atoms e.g. formyloxy, acetoxy or propinoxy. The term "5 or 6 membered heterocyclic ring" preferably refers to a pyrrolidinyl, piperidino, morpholino, piperazinyl or N-substituted piperazinyl group.

Preferred classes of compounds are those in which the following groups have the meanings given $R_1$ = hydrogen, hydroxyl, halogen particularly chlorine, alkyl particularly methyl, alkoxy particularly ethoxy or isopropoxy, alkenyloxy particularly allyloxy, alkoxyalkoxy particularly 2 - methoxyethoxy, hydroxyalkoxy particularly 2 - hydroxyethoxy, dialkylaminoalkoxy particularly 2 - dimethylaminoethoxy, alkylamino particularly butylamino, dialkylamino particularly dimethylamino, aralkylamino particularly benzylamino, alkoxyalkylamino particularly 2 - methoxyethylamino, hydroxyalkylamino particularly 2 - hydroxyethylamino, aminoalkylamino particularly 2 - aminoethylamino, dialkylaminoalkylamino particularly 2 - dimethylaminoethylamino, piperidino, morpholino or an N-methylpiperazinyl group.

$R_2$ = hydrogen, alkyl particularly ethyl or isopropyl, alkenyl particularly allyl, alkoxyalkyl particularly 2 - methoxyethyl, acyloxyalkyl particularly 2 - formyloxyethyl, hydroxyalkyl particularly 2 - hydroxyethyl, aminoalkyl particularly 2 - aminoethyl, alkylaminoalkyl particularly 2 - methylaminoethyl, dialkylaminoalkyl, particularly 2 - dimethylaminoethyl, alkylaralkylamino alkyl, particularly 2 - methylbenzylaminoethyl, diaralkylaminoalkyl particularly 2 - dibenzylaminoethyl.

Specific preferred compounds according to the invention are those the preparation of which is described in the Examples.

The invention includes salts of compounds of structures (I) and (II). Salts may be formed with inorganic or organic bases, particularly those of alkali metals e.g. sodium and with organic bases such as dimethylaminoethanol. When basic centres are present, addition salts may also be formed with organic or inorganic acids.

When $R_2$ = H the compounds (I) may exist in tautomeric equilibrium with structures of formula (II) and the latter are also understood to fall within the scope of the present invention.

The compounds of the invention show promise as agents for the treatment of conditions in which combinations of an antigen with a reaginic antibody is primarily responsible, for example, extrinsic asthma, hay fever, urticaria, eczema or atopic dermatitis. Thus 1-ethyl-1,4-dihydro-7-methyl-4-oxo-1,8-naphthyridine-3-carboxamide (Example 1) was compared with disodium cromoglycate, which is known to be effective in the prophylactic treatment of asthma. It was shown to be about 75 times as active as disodium cromoglycate in inhibiting release of histamine in the passive peritoneal anaphylaxis induced in rats with the DNP-egg albumen system (J. Exp. Med. 1969, 127, 727).

The invention also provides pharmaceutical compositions which contain a compound of general formula (I) or a salt thereof together with a pharmaceutically acceptable carrier, excipient, or other formulatory agent. The compositions may also contain supplementary medicinal agents, e.g. broncho-dilators. Suitable forms of oral administration include tablets, capsules, syrups, or emulsions. For administration by inhalation the compositions according to the invention may be in the form of a powder or snuff or as an aerosol spray presentation. The latter may conveniently be a pressurised pack with a metering valve to deliver a fixed dosage unit or may be an aqueous solution delivered via a nebuliser.

The dosage at which the active ingredient is administered may vary within a wide range, depending on the age, weight and condition of the patient. A suitable oral dosage range is generally from 2–1500 mg and for inhalation is from 0.1–20 mg. The dose may be repeated if required.

The invention also provides a process for the preparation of compounds of formula I in which a 1,8-naphthyridine-3-carboxylic acid of formula (III) or an activated derivative thereof, wherein $R_1$ and $R_2$ have the meanings stated above or are convertible there into, is condensed with 5-aminotetrazole (IV):

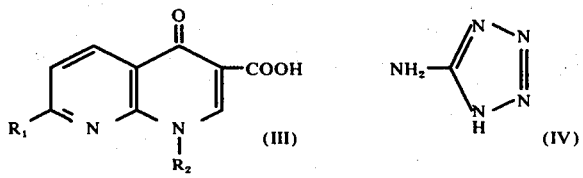

(III)  (IV)

The condensation of a 1,8-naphthyridine-3-carboxylic acid (III) with 5-aminotetrazole (IV) may be effected with the aid of a variety of condensing agents which are of general application for the formation of amide bonds. One such reagent, N,N'-carbonyldiimidazole, is particularly useful and condensations using this reagent are preferably carried out in an aprotic solvent such as tetrahydrofuran and/or dimethylformamide. The reaction may be carried out at ambient or elevated temperatures e.g. 20°–120° C.

Suitable activated derivatives of the 1,8-naphthyridine carboxylic acids (III) include the acid halides, preferably the acid chlorides or mixed anhydrides, preferably the mixed anhydride derived from the acid (III) and an alkyl carbonic acid derivative e.g. ethylcarbonic acid $C_2H_5OCOOH$.

The condensation of an acid chloride derived from a 1,8-naphthyridine carboxylic acid (III) with 5-aminotetrazole is preferably carried out in an aprotic solvent such as dioxan or tetrahydrofuran, and is also preferably carried out in the presence of an acid acceptor for example a tertiary organic base, such as pyridine, or triethylamine; or in an aqueous medium and in the presence of an inorganic base such as an alkali metal hydroxide, carbonate or bicarbonate e.g. sodium or potassium hydroxide, sodium or potassium carbonate or bicarbonate.

When a mixed anhydride is used as the activated derivative the reaction may also be carried out in a polar aprotic solvent such as dimethylformamide, at a reaction temperature which is preferably below 10° C.

Compounds of the invention may also be converted into other compounds of the invention. For example, compounds (I) in which $R_2$ = an acyloxyalkyl group e.g. formyloxyalkyl may be converted into compounds in which $R_2$ = hydroxyalkyl by hydrolysis, preferably with aqueous alkali, particularly aqueous sodium or potassium hydroxide. Compounds of formula I in which $R_1$ is chlorine may be converted into compounds of formula I in which $R_1$ is a group $OR_3$ in which $R_3$ has the meanings given by treatment with an alkali metal alkoxide $MOR_3$ in which M represents an alkali metal atom e.g. sodium alkoxide, $R_3ONa$ and this reaction is preferably carried out in an excess of the alcohol $R_3OH$ as solvent. Also compounds of formula I in which $R_1$ is halogen preferably chlorine may be converted into compounds of formula I in which $R_1$ is the group $NR_3R_4$ by treatment with the amine $R_3R_4NH$. If desired these reactions may be carried out in the presence of a solvent, for example water or an alcohol e.g. ethanol. The displacement reactions involving the group $R_1$ = halogen are preferably carried out at an elevated temperature.

Compounds of the general formula I in which $R_2$ = a dibenzylaminoalkyl or benzylalkylaminoalkyl group may be converted into compounds in which $R_2$ = aminoalkyl or alkylaminoalkyl group by hydrogenolysis, for example with hydrogen and a noble metal catalyst such as palladium.

The starting 1,8-naphthyridine-3-carboxylic acids (III) are either known compounds or may be prepared by standard literature routes (R. C. Elderfield, Heterocyclic Compounds, Vol. 7 John Wiley and Sons Inc. 1952, 203 and BP. 1,000,892). One such route for the preparation of compound III where $R_1$ is other than hydrogen is outlined below:

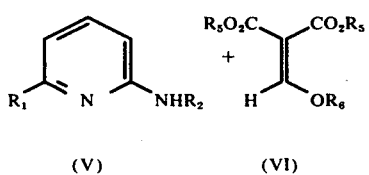
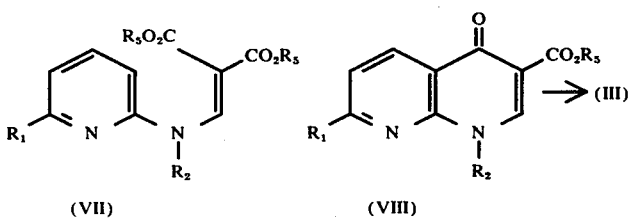

(V)  (VI)  (VII)  (VIII)

The reaction of the aminpyridine (V) with the alkyl alkoxymethylenemalonate (VI) in which $R_5$ and $R_6$ = alkyl gives the aminoester (VII) which may be cyclised to the 1,8-naphthyridine carboxylic ester (VIII), for example by heating in an inert solvent, e.g. diphenyl ether. Alkaline hydrolysis of the ester (VIII) gives the required 1,8-naphthyridine-3-carboxylic acid (III).

The groups $R_1$ and $R_2$ may be introduced at any convenient point in the synthesis of the acid (III) or ester (VIII). Thus for example where the groups $R_2$ is other than hydrogen it may be present throughout or may be obtained by alkylation of the ester (VIII) $R_2$ = H with conventional alkylating agents, for example an alkyl halide or dialkyl sulphate. This reaction may be advantageously carried out in a solvent such as 2-butanone or dimethylformamide and in the presence of an alkali metal carbonate such as potassium carbonate; the reaction is preferably carried out at elevated temperatures, for example, between 50°–100° C. Alkaline hydrolysis of the alkylation product gives the required acid (III).

1,8-naphthyridine-3-carboxylic acids (III) (in which $R_1$ = halogen) are advantageously prepared by the reaction of the acid (III, $R_1$ = OH) with a phosphoryl halide e.g. phosphoryl chloride and preferably at an elevated reaction temperature e.g. 100° C.

1,8-Naphthyridine-3-carboxylic acids (III), (in which $R_1$ = H) may be prepared by hydrogenolysis of the corresponding acid (III) in which $R_1$ = Cl, using hydrogen and a noble metal catalyst e.g. palladium.

The acid halide derived from the acid (III) may be prepared from the acid in the conventional manner e.g. reaction with thionyl chloride, or a phosphorus pentahalide such as $PCl_5$.

The mixed anhydrides derived from the acid (III) may be prepared in a conventional manner. For example a suitable acid halide e.g. ethyl chloroformate is added to a mixture of the acid (III) and a tertiary organic base such as triethylamine, in a polar aprotic solvent such as dimethylformamide. Preferably the reaction is carried out in the cold e.g. between −10° to 10° C.

The following Examples illustrate the invention.

EXAMPLE 1

1-Ethyl-1,4-dihydro-7-methyl-4-oxo-N(1H-tetrazol-5-yl)-1,8-naphthyridine-3-carboxamide 1-Ethyl-1,4-dihydro-7-methyl-4-oxo-1,8-naphthyridine-3-carboxylic acid (4.1g) and N,N′-carbonyldiimidazole (2.85g) in dimethylformamide (30 ml) were stirred and heated at 100° for 3 hours and cooled. 5-Amino-1H-tetrazole (3.6 g) was added and the mixture was stirred at room temperature for 16 hours. The solid was collected and dissolved in aqueous dimethylaminoethanol and the solution was acidified to pH2 with dilute hydrochloric acid. The solid was filtered off and dried, m.p. above 289° (d), (60%)

EXAMPLE 2

1,4-Dihydro-7-methyl-4-oxo-N(1H-tetrazol-5-yl)-1,8-naphthyridine-3-carboxamide 1,4-Dihydro-7-methyl-4-oxo-1,8-naphthyridine-3-carboxylic acid (4 g) and N,N′-carbonyldiimidazole (3.5 g) in dimethylformamide (40 ml) were heated at 80° for 6 hours. 5-Amino-1H-tetrazole (2.5 g) was added and the mixture was stirred and heated at 80° for 1.5 hours. The solid was collected and dissolved in aqueous sodium hydroxide. The solution was acidified with glacial acetic acid and the solid was collected and dried. It had m.p. 344°–345.5°, (47%)

EXAMPLE 3

1(2-Dimethylaminoethyl)-1,4-dihydro-7-methyl-4-oxo-N(1H-tetrazol-5-yl)-1,8-naphthyridine-3-carboxamide a. 1(2-Dimethylaminoethyl)-1,4-dihydro-7-methyl-4-oxo-1,8-naphthyridine-3-carboxylic acid, ethyl ester 1,4-Dihydro-7-methyl-4-oxo-1,8-naphthyridine-3-carboxylic acid, ethyl ester (8.8 g) 2-dimethylaminoethyl chloride, hydrochloride (11 g) and anhydrous potassium carbonate (52.5 g) in butanone were stirred and heated under reflux for 22 hours. The solid was filtered off, the solvent removed and the residue was crystallized from light petroleum (b.p. 60°–80°, 100 ml). The product had m.p. 74°–78° (96%).

The following compounds were made in a similar manner from 1,4-dihydro-7-methyl-4-oxo-1,8-naphthyridine-3-carboxylic acid, ethyl ester and the alkylating agent quoted in the brackets.

1-[2-(Benzylmethylamino)ethyl]-1,4-dihydro-7-methyl-4-oxo-1,8-naphthyridine-3-carboxylic acid, ethyl ester, a red oil that did not crystallise (2-(Benzylmethylaminoethyl bromide).

1-[2-(Dibenzylamino)ethyl]-1,4-dihydro-7-methyl-4-oxo-1,8-naphthyridine-3-carboxylic acid, ethyl ester, m.p. 170°–174° (72%) (2-Dibenzylaminoethyl bromide).

1,4-Dihydro-7-methyl-4-oxo-1-(2-phenylethyl)-1,8-naphthyridine-3-carboxylic acid, ethyl ester, an oil that did not crystallise (2-phenethyl bromide).

1,4-Dihydro-1-isopropyl-7-methyl-4-oxo-1,8-naphthyridine-3-carboxylic acid, ethyl ester, a brown solid not further purified (isopropyl bromide).

b. 1(2-Dimethylaminoethyl)-1,4-dihydro-7-methyl-4-oxo-1,8-naphthyridine-3-carboxylic acid, hydrochloride 1-(2-Dimethylaminoethyl)-1,4-dihydro-7-methyl-4-oxo-1,8-naphthyridine-3-carboxylic acid, ethyl ester (11 g) and sodium hydroxide (2.9 g) in water (110 ml) and ethanol (110 ml) were heated under reflux for 2 hours. The solution was concentrated to 60 ml and acidified to pH6 with dilute hydrochloric acid. The solid was collected and dried, m.p. 234°–236° (47%).

The following compounds were prepared in a similar manner from the corresponding ethyl esters disclosed in Example 3 (a) above.

1-[2-(Benzylmethylamino)ethyl]-1,4-dihydro-7-methyl-4-oxo-1,8-naphthyridine-3-carboxylic acid, m.p. 157°–157.5° (80%).

1-[2-(Dibenzylamino)ethyl]-1,4-dihydro-7-methyl-4-oxo-1,8-naphthyridine-3-carboxylic acid, m.p. 177°–179.5° (72%).

1,4-Dihydro-7-methyl-4-oxo-1-(2-phenylethyl)-1,8-naphthyridine-3-carboxylic acid, m.p. 234°–235° (44%).

1,4-Dihydro-1-isopropyl-7-methyl-4-oxo-1,8-naphthyridine-3-carboxylic acid, m.p. 240°–241° (d) 913%).

c. 1(2-Dimethylaminoethyl)-1,4-dihydro-7-methyl-4-oxo-N(1H-tetrazol-5-yl)-1,8-naphthyridine-3-carboxamide 1(2-Dimethylaminoethyl)-1,4-dihydro-7-methyl-4-oxo-1,8-naphthyridine-3-carboxylic acid, hydrochloride (4.6 g) and N,N′-carbonyldiimidazole (2.75 g) in dimethylformamide (40 ml) were stirred and heated to 90° for 2 hours. 5-Amino-1H-tetrazole (1.45 G) was added and the mixture was heated to 40° and stirred for 36 hours. The solid was collected, m.p. 305°–307° (d). (39%).

The following compounds were prepared in a similar manner from the corresponding acids described in Example 3 (b) above.

1-[2-(Benzylmethylamino)ethyl]-1,4-dihydro-7-methyl-4-oxo-N(1H-tetrazol-5-yl)-1,8-naphthyridine-3-carboxamide, m.p. 275°–280° (d) (62%).

1-[2-(Dibenzylamino)ethyl]-1,4-dihydro-7-methyl-4-oxo-N(1H-tetrazol-5-yl)-1,8-naphthyridine-3-carboxamide, m.p. 269.269.5° (41%).

1,4-Dihydro-7-methyl-4-oxo-1-(2-phenyl)-N(1H-tetrazol-5-yl)-1,8-naphthyridine-3-carboxamide, m.p. 325° (d) (74%).

1,4-Dihydro-1-isopropyl-7-methyl-4-oxo-N(1H-tetrazol-5-yl)-1,8-naphthyridine-3-carboxamide, m.p. > 300° (d), (36%).

EXAMPLE 4

1.

1(2-Formyloxyethyl)-1,4-dihydro-7-methyl-4-oxo-N(1H-tetrazol-5-yl)-1,8-naphthyridine-3-carboxamide a. 1(2-Formyloxyethyl)-1,4-dihydro-7-methyl-4-oxo-1,8-naphthyridine-3-carboxylic acid Formic acid (1.1 ml) was added to acetic anhydride (2.2 ml) which was cooled to 0°–5°. The mixture was heated at 50° for 15 minutes, cooled to 0° and added to 1,4-dihydro-1(2-hydroxyethyl)-7-methyl-4-oxo-1,8-naphthyridine-3-carboxylic acid (1.5 g) in pyridine (12 ml), also cooled to 0°. The mixture warmed to room temperature and after 1 hour the solid was collected, washed with pyridine and dried, m.p. 213°–214° (85%).

b. 1(2-Formyloxyethyl)-1,4-dihydro-7-methyl-4-oxo-N(1H-tetrazol-5-yl)-1,8-naphthyridine-3-carboxamide 1(2-formyloxyethyl)-1,4-dihydro-7-methyl-4-oxo-1,8-naphthyridine-3-carboxylic acid (1.3 g) and N,N'-carbonyldiimidazole (0.8 g) in dimethylformamide (25 ml) were heated at 80° for 5 hours. 5-Amino-1H-tetrazole (0.45 g) was added and the mixture was stirred at 80° for 1 hour. The solid was collected and dried, m.p. 268.5°–269° (d), (40%).

2. 1-Allyl-1,4-dihydro-7-methyl-4-oxo-N(1H-tetrazol-5-yl)-1,8-naphthyridine-3-carboxamide, m.p. 326°–327°, was similarly prepared from 1-Allyl-1,4-dihydro-7-methyl-4-oxo-1,8-naphthyridine-3-carboxylic acid (75%).

EXAMPLE 5

1,4-Dihydro-1(2-hydroxyethyl)-7-methyl-4-oxo-N(1H-tetrazol-5-yl)-1,8-naphthyridine-3-carboxamide 1,4-Dihydro-1(2-formyloxyethyl)-7-methyl-4-oxo-N(1H-tetrazol-5yl)-1,8-naphthyridine-3-carboxamide (Example 4(1)) (0.5 g) in aqueous sodium hydroxide (3.5 ml), 2N was heated on a steam bath for 10 minutes. The solution was acidified to pH 1 with a dilute hydrochloric acid and the solid was collected and dried, m.p. 315°–316° (d), (32%).

EXAMPLE 6

7-Ethoxy-1,4-dihydro-4-oxo-N(1H-tetrazol-5-yl)-1,8-naphthyridine-3-carboxamide

7-Ethoxy-1,4-dihydro-4-oxo-1,8-naphthyridine-3-carboxylic acid (1.9 g) and N,N-carbonyldiimidazole (2 g) in dimethylformamide (50 ml) were stirred and heated at 100° for 4 hours. 5-Amino-1H-tetrazole (2.1 g) was added and the mixture stirred and heated at 100° for 30 minutes, and cooled. The solid was collected and dissolved in hot (60°) dilute sodium hydroxide and the solution was neutralised (pH 7) with dilute hydrochloric acid. The solid was collected, washed with water and dried, m.p. above 319° (d), (75%).

EXAMPLE 7

1,4-Dihydro-7-hydroxy-4-oxo-N(1H-tetrazol-5-yl)-1,8-naphthyridine-3-carboxamide, compound with imidazole 1,4-Dihydro-7-hydroxy-4-oxo-1,8-naphthyridine-3-carboxylic acid (2 g) and N,N'-carbonyldiimidazole (2.3 g) in anhydrous dimethylformamide (20 ml) were heated to 100° for 1 hour. 5-Amino-1H-tetrazole was added and the mixture was heated at 90° for a further hour and cooled. The solid was collected and dried. It had m.p. > 300°.

EXAMPLE 8

1. 7-Ethoxy-1-ethyl-1,4-dihydro-4-oxo-N(1H-tetrazol-5-yl)-1,8-naphthyridine-3-carboxamide 7-Ethoxy-1-ethyl-1,4-dihydro-4-oxo-1,8-naphthyridine-3-carboxylic acid (2.0 g) and N,N'-carbonyldiimidazole (1.85 g) in dimethylformamide (40 ml) were stirred and heated to 100° for 7 hours. 5-Amino-1H-tetrazole (1.3 g) was added and the mixture heated at 100° for 1 hour and cooled. The solid was collected and dissolved in hot aqueous dimethylaminoethanol (20 ml, 5%). The hot solution was acidified with hydrochloric acid and the solid was filtered off, washed with water and dried, m.p. above 307° (d), (61%).

The following compounds were prepared in a similar manner:

2. 1-Ethyl-1,4-dihydro-7-hydroxy-4-oxo-N(1H-tetrazol-5-yl)-1,8-naphthyridine-3-carboxamide m.p. 312° (d) (19%) from 1-ethyl-1,4-dihydro-7-hydroxy-4-oxo-1,8-naphthyridine-3-carboxylic acid.

3. 1-Ethyl-1,4-dihydro-4-oxo-N(1H-tetrazol-5-yl)-1,8-naphthyridine-3-carboxamide, m.p. 315°–317° (82%) from 1-ethyl-1,4-dihydro-4-oxo-1,8-naphthyridine-3-carboxylic acid.

EXAMPLE 9

7-Ethoxy-1,4-dihydro-1(2-hydroxyethyl)-4-oxo-N(1H-tetrazol-5-yl)-1,8-naphthyridine-3-carboxamide a. 7-Ethoxy-1,4-dihydro-1(2-hydroxyethyl)-4-oxo-1,8-naphthyridine-3-carboxylic acid 7-Ethoxy-1,4-dihydro-4-oxo-1,8-naphthyridine-3-carboxylic acid, ethyl ester (3.6 g), 2-bromoethanol and potassium carbonate (7.5 g) in dimethylformamide (50 ml) (4.95 ml) were stirred and heated on a steam bath for 16 hours. The solid was filtered off and the filtrate evaporated. The residue was crystallized from dimethylformamide. This ester (2.0 g) and aqueous sodium hydroxide (40 ml, 2N) were heated on a steam bath for 3 hours, cooled and acidified to pH 2 with aqueous hydrochloric acid. The solid was collected and crystallized from ethanol, m.p. 219.5°–220° (24%).

b. 7-Ethoxy-1(2-formyloxyethyl)-1,4-dihydro-4-oxo-1,8-naphthyridine-3-carboxylic acid Formic acid (1 ml) was added to acetic anhydride (2 ml) which was cooled to 0°. The mixture was warmed to 50° for 15 minutes, cooled to 0° and added to a suspension of 7-ethoxy-1,4-dihydro-1-hydroxyethyl-4-oxo-1,8-naphthyridine-3-carboxylic acid (0.78 g) in dry pyridine (10 ml). The mixture was stirred at 0° for 45 minutes and then for 1 hour at room temperature. The solid was collected and washed with water and dried, m.p. 208.5°–210° (d). (71%).

c. 7-Ethoxy-1,4-dihydro-1(2-hydroxyethyl)-4-oxo-N(1H-tetrazol-5-yl)-1,8-naphthyridine-3-carboxamide 7-Ethoxy-1(2-formyloxyethyl)-1,4-dihydro-4-oxo-1,8-naphthyridine-3-carboxylic acid (0.5 g) and N,N'-carbonyldiimidazole (0.4 g) in dimethylformamide (10 ml) were stirred and heated to 80° for 6 hours. 5-Amino-1H-tetrazole (0.42 g) was added and the mixture stirred and heated to 80° for 30 minutes. The solid was collected and dissolved in aqueous sodium hydroxide (10 ml, 2N) and the solution was acidified to pH 1 with dilute hydrochloric acid. The solid was filtered off, washed with water and dried, m.p. above 297° (d). (45%).

EXAMPLE 10

7-Chloro-1,4-dihydro-4-oxo-N(1H-tetrazol-5-yl)-1,8-naphthyridine-3-carboxamide a. 7-Chloro-1,4-dihydro-4-oxo-1,8-naphthyridine-3-carboxylic acid 1,4-Dihydro-7-hydroxy-4-oxo-1,8-naphthyridine-3-carboxylic acid (10 g) and phosphoryl chloride (20 ml) were stirred and heated at 100° for 2.5 hours. The mixture was cooled and poured into iced water (800 ml). The solid was filtered off and crystallized from dimethylformamide, m.p. 271°–273° (87%).

b. 7-Chloro-1,4-dihydro-4-oxo-N(1H-tetrazol-5-yl)-1,8-naphthyridine-3-carboxamide 7-Chloro-1,4-dihydro-4-oxo-1,8-naphthyridine-3-carboxylic acid, (1 g) and N,N'-carbonyldiimidazole (1.1g) in dimethylformamide (12 ml) were heated at 100° for 1 hour. 5-Amino-1H-tetrazole (0.95 g) was added and the mixture was heated at 100° for 1 hour and cooled. The solid was filtered off and stirred with aqueous hydrochloric acid (10 ml, 2N) and the solid was collected and dried, m.p. above 350°.

EXAMPLE 11

7-Chloro-1-ethyl-1,4-dihydro-4-oxo-N(1H-tetrazol-5-yl)-1,8-naphthyridine-3-carboxamide.

Method A

7-Chloro-1-ethyl-1,4-dihydro-4-oxo-1,8-naphthyridine-3-carboxylic acid (10 g) and N,N'-carbonyldiimidazole (8 g) in dimethylformamide (100 ml) were stirred and heated to 100° for 2 hours. 5-Amino-1H-tetrazole (10 g) and tetrahydrofuran (100 ml) were added and the mixture was heated under reflux for 30 minutes. The solid was collected and stirred with dilute aqueous hydrochloric acid (500 ml) (0.1 N). The solid was filtered off and dried, m.p. above 400°.

Method B a. 7-Chloro-1-ethyl-1,4-dihydro-4-oxo-1,8-naphthyridine-3-carbonyl chloride 7-Chloro-1-ethyl-1,4-dihydro-4-oxo-1,8-naphthyridine-3-carboxylic acid (29.5 g) and thionyl chloride (18 ml) in dry toluene (900 ml) were stirred and heated under reflux for 1 hour. The solution was cooled and the solid that separated was collected. It had m.p. 186.5°–188.5° (98%).

b. 7-Chloro-1-ethyl-1,4-dihydro-4-oxo-N(1H-tetrazol-5yl)-1,8-naphthyridine-3-carboxamide 7-Chloro-1-ethyl-1,4-dihydro-4-oxo-1,8-naphthyridine-3-carbonyl chloride (22.3 g) in dry dioxan (350 ml) was added slowly to 5amino-1H-tetrazole (7.9 g) and triethylamine (15.1 ml) in dry dioxan (350 ml) and the mixture kept 3 days at room temperature. The solid was collected and dissolved in aqueous dimethylaminoethanol. The solution was filtered and acetic acid was added to the filtrate. The solid that separated was collected and had m.p. above 400°.

EXAMPLE 12

1.

1-Ethyl-1,4-dihydro-7[(2-hydroxyethyl)amino]-4-oxo-N(1H-tetrazol)-5-yl)-1,8-naphthyridine-3-carboxamide 7-Chloro-1-ethyl-1,4-dihydro-4-oxo-N(1H-tetrazol-5-yl)-1,8-naphthyridine-3-carboxamide (Example 11, 0.5 g) and 2-aminoethanol (10 ml) in ethanol (10 ml) were heated under reflux for 1.5 hours. The solution was cooled and acidified to pH 1 with 2N hydrochloric acid. The solid was collected and dissolved in dimethyl sulphoxide and the solution was diluted with water. The solid was collected and dried, m.p. 300°–304° (d) (37%).

The following compounds were prepared in a similar manner from 7-chloro-1-ethyl-1,4-dihydro-4-oxo-(1H-tetrazol-5-yl)-1,8-naphthyridine-3carboxamide and the amine quoted:

(2) 7-Benzylamino-1-ethyl-1,4-dihydro-4-oxo-N(1H-tetrazol-5-yl)-1,8-naphthyridine-3-carboxamide, m.p. 315.5°–317° (d) (66%), with benzylamine.

3. 1-Ethyl-1,4-dihydro-7-(4-methyl-1-piperazinyl)-4-oxo-N(1H-tetrazol-5-yl)-1,8-naphthyridine-3-carboxamide, hydrochloride, m.p. 313° (d) (29%), with N-methylpiperazine.

4. 1-Ethyl-1,4-dihydro-7-(2-methoxyethylamino)-4-oxo-N(1H-tetrazol-5-yl)-1,8-naphthyridine-3-carboxamide, m.p. 295°–298° (d) (66%), with 2-methoxyethylamine.

5. 1-Ethyl-1,4-dihydro-7-morpholino-4-oxo-N(1H-tetrazol-5-yl)-1,8-naphthyridine-3-carboxamide, m.p. 314°–317° (d) (70%) with morpholine.

EXAMPLE 13

1.

7(2-Dimethylaminoethylamino)-1-ethyl-1,4-dihydro-4-oxo-N(1H-tetrazol-5-yl)-1,8-naphthyridine-3-carboxamide 7-Chloro-1-ethyl-1,4-dihydro-4-oxo-N(1H-tetrazol-5-yl)-1,8-naphthyridine-3-carboxamide (Example 11, 1 g), 2-dimethylaminoethylamine (5 ml) and water (2 ml) were heated on a steam bath for 5.5 hours. The mixture was concentrated under reduced pressure to give an oil. The oil was triturated with ether and the solid was collected, m.p. 294°–296°, 27%.

The following compounds were prepared in a similar manner from 7-chloro-1-ethyl-1,4-dihydro-4-oxo-N(1H-tetrazol-5-yl)-1,8-naphthyridine-3-carboxamide and the amine quoted:

2. 7-Dimethylamino-1-ethyl-1,4-dihydro-4-oxo-N(1H-tetrazol-5-yl)-1,8-naphthyridine-3-carboxamide, m.p. 330° (d) (51%), from dimethylamine.

3. 7-Butylamino-1-ethyl-1,4-dihydro-4-oxo-N(1H-tetrazol-5-yl)-1,8-naphthyridine-3-carboxamide, m.p. 322°–323° (d) (100%) from n-butylamine.

4. 7-(2-Aminoethylamino)-1,4-dihydro-1-ethyl-4-oxo-N(1H-tetrazol-5-yl)-1,8-naphthyridine-3-carboxamide, m.p. 289°–292° (d) (97%) from 1,2-diaminoethane.

5. 1-Ethyl-1,4-dihydro-4-oxo-7-piperidino-N(1H-tetrazol-5-yl)-1,8-naphthyridine-3-carboxamide, m.p. 328° (d) (56%), from piperidine.

EXAMPLE 14

1.

1-Ethyl-1,4-dihydro-7-(2-hydroxyethoxy)-4-oxo-N(1H-tetrazol-5-yl)-1,8-naphthyridine-3-carboxamide 7-Chloro-1-ethyl-1,4-dihydro-4-oxo-N(1H-tetrazol-5yl)-1,8-naphthyridine-3-carboxamide (Example 11, 1 g) was added to a solution of sodium (0.14 g) in ethane-1,2-diol (10 ml) and the mixture was heated at 100° for 25 hours. The mixture was cooled and acidified with glacial acetic acid and the solid was collected. The solid was dissolved in aqueous dimethylaminoethanol (20 ml, 5%) and the solution was acidified with glacial acetic acid. The solid was collected and dried, m.p. 310–3° (56%).

The following compounds were prepared in a similar manner from 7-chloro-1-ethyl-1,4-dihydro-4-oxo-N(1H-tetrazol-5-yl)-1,8-naphthyridine-5-carboxamide and the sodio derivative of the alcohol quoted:

2. 7-Allyloxy-1-ethyl-1,4-dihydro-4-oxo-N(1H-tetrazol-5-yl)-1,8-naphthyridine-3-carboxamide, m.p. 274°–275° (d) (82%) from allyl alcohol.

3. 1,4-Dihydro-7-(2-dimethylaminoethoxy)-1-ethyl-4-oxo-N(1H-tetrazol-5-yl)-1,8-naphthyridine-3-carboxamide hydrochloride, m.p. 265.5°–267° (d) (32%) from 2-dimethylaminoethanol.

4. 1-Ethyl-1,4-dihydro-7-isopropyl-4-oxo-N(1H-tetrazol-5-yl)-1,8-naphthyridine-3-carboxamide, m.p. 290°–300°(d) (87%), from isopropanol.

5. 1-Ethyl-1,4-dihydro-7-(2-methoxyethoxy)-4-oxo-N(1H-tetrazol-5-yl)-1,8-naphthyridine-3-carboxamide, m.p. 288.5°–289.5° (62%), from 2-methoxyethanol.

EXAMPLE 15

1,4-Dihydro-1-isopropyl-7-methyl-4-oxo-N(1H-tetrazol-5-yl)-1,8-naphthyridine-3-carboxamide 1,4-Dihydro-1-isopropyl-7-methyl-4-oxo-1,8-naphthyridine-3-carboxylic acid (Example 3b, 0.9 g) was warmed in dimethylformamide (70 ml) and triethylamine (0.7 ml) was added. The solution was cooled to 0° and ethyl chloroformate (0.4 ml) was added and the mixture was kept for 30 minutes. 5-Amino-1H-tetrazol (3.6 g) was added and the mixture was stirred at room temperature for 18 hours and filtered. The filtrate was evaporated and the residue was crystallised from a mixture of dimethylformamide and isopropanol. The product has m.p. > 300° (d) (36%).

EXAMPLE 16

1,4-Dihydro-1(2-methoxyethyl)-7-methyl-4-oxo-N(1H-tetrazol-5-yl)-1,8-naphthyridine-5-carboxamide a. 1,4-Dihydro-1-(2-methoxyethyl)-7-methyl-4-oxo-1,8-naphthyridine-5-carboxylic acid 1,4-Dihydro-1-(2-hydroxyethyl)-7-methyl-4-oxo-1,8-naphthyridine-3-carboxylic acid (1 g) in ethanol (30 ml) and aqueous sodium hydroxide (10 ml, 40%) was treated alternatively with dimethyl sulphate (5 ml) and aqueous sodium hydroxide (10 ml, 40%) until dimethylsulphate (25 ml) had been added. The mixture was refluxed for 1.5 hours and concentrated to a volume of 20 ml. Concentrated hydrochloric acid was added and the solid was collected and washed with water and dried. The product had m.p. 244°–245° (d).

h. 1,4-Dihydro-1-(2-methoxyethyl)-7-methyl-4-oxo-N(1H-tetrazol-5-yl)-1,8-naphthyridine-3-carboxamide 1,4-Dihydro-1-(2-methoxyethyl)-7-methyl-4-oxo-1,8-naphthyridine-3-carboxylic acid (0.5 g) and N,N'-carbonyldiimidazole (0.31 g) in dimethylformamide (50 ml) were warmed at 60° for 1 hour. 5-Amino-1H-tetrazol (0.16 g) was added and the solution was stirred at 60° for 2 hours and cooled. The solid was collected and crystallised from dimethylformamide and had m.p. 245°–246° (d).

EXAMPLE 17

1-(2-Aminoethyl)-1,4-dihydro-7-methyl-4-oxo-N(1H-tetrazol-5-yl)-1,8-naphthyridine-3-carboxamide, hydrochloride, monohydrate 1-(2-Dibenzylaminoethyl)-1,4-dihydro-7-methyl-4-oxo-N(1H-tetrazol-5-yl)-1,8-naphthyridine-5-carboxamide (Example 5e, 1.2 g) in aqueous dimethylaminoethanol (100 ml) was shaken with hydrogen at room temperature and atmospheric pressure in the presence of palladium on charcoal catalyst (0.2 g, 10%) for 48 hours. The catalyst was filtered off and the filtrate was evaporated. The residue was dissolved in 2N sodium hydroxide and the solution was acidified with 5N hydrochloric acid. The solid that separated was collected and dried. It had m.p. 315° (d).

EXAMPLE 18

1-Ethyl-1,4-dihydro-7-methyl-4-oxo-N(1H-tetrazol-5-yl)-1,8-naphthyridine-3-carboxamide, sodium salt, monohydrate 2N Sodium hydroxide was added dropwise to 1ethyl-1,4-dihydro-7-methyl-4-oxo-N(1H-tetrazol-5-yl)-1,8-naphthyridine-3-carboxamide (Example 1, 1g) in water (50 ml) until the solution had a pH of 9. The solution was concentrated to one quarter of its volume and acetone (30 ml) was added. The solid that crystallised was collected and dried. It had m.p. 250° (d).

EXAMPLE 19

(Pharmaceutical compositions)

Inhalation aerosol

To prepare 100 aerosol cans, each of which delivers 200 metered doses of 1.0 mg All 10429+

Micronise the AH 10429V++ to give a powder in which nearly all the particles are smaller than 5 μm in diameter. Dissolve 0.60 g of Emulsifier YN 100 in 570 g of trichlorofluoromethane (Areton 11) at 10° C. Disperse in this solution with a high shear mixer 28.6 g of micronised All 10429V. Meter 5.7 g fractions of the drug suspension into suitable aluminium cans and seal the cans by crimping on suitable pressure-filling aerosol valves capable of metering 85 mg doses of final product. Inject through the valve into each can 14.7 g of dichlorodifluoromethane (Areton 12). Fit a suitable oral adaptor/actuator unit on to each can.

**Emulsifier YN 100 is a grade of the ammonium salt synthetic lecithin, supplied by Cadbury Bros.
+ AH 10429 is the product of Example 1.
++ AH 10429V is the sodium salt monohydrate of All 10429. The production of this salt is described in Example 18.

Tablets

To prepare 10,000, each containing 200 mg AH 10429

Mix together 2.20 kg All 10429V (sieved 60 mesh) with 2.00 kg lactose, B.P. and 100 g of maize starch. Evenly moisten the mixed powders with sufficient water to produce a cohesive mass, pass this through a 16 mesh sieve and dry the granules at 50° C in a fluidised bed dryer. Blend the dry granules with 100 g of maize starch and 10 g of magnesium stearate. Compress on a suitable tablet press to give tablets each weighing 440 mg.

Capsules (for oral use)

To prepare 10,000 hard gelatin capsules containing AH 10429

Mix the powdered AH 10429V (sieved 60 mesh) with sufficient Sta-Rx starch* 1500 and magnesium stearate equivalent to 1% of the total powder-weight, to give the required dosage, which can be up to 250 mg AH 10429. Fill into No. 1 hard gelatin capsules with a suitable capsulating machine.

* Sta-Rx starch 1500 is a grade of free-flowing starch supplied by A. E. Staley Co. Ltd., London.

Capsules for Inhalation

To prepare 10,000 capsules each containing 20 mg AH 10429. for use in an insufflator for inhalation into the lung.

Micronise the All 10429V to give a powder in which nearly all particles are smaller than 5 μm diameter.

Blend 220 g of micronised drug with 200 g of lactose B.P., previously sieved through 200 mesh and over 300 mesh sieves. Fill the powder blend into No. 3 hard gelatin capsules on a suitable machine, so that each capsule contains 42 mg of powder.

AH 10429 (or 10429V) may be replaced by another compound according to the invention if desired.

We claim:

1. A compound of the formula

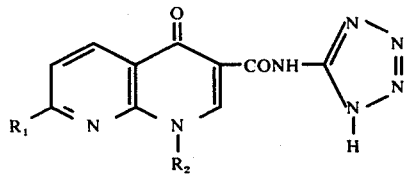

or the formula

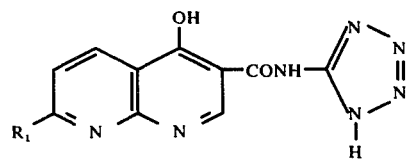

in which $R_1$ represents pyrrolidinyl, piperidino, morpholino, piperazinyl or N-methyl-piperazinyl group, and $R_2$ represents a hydrogen atom, a $C_{2-6}$ alkenyl group, a $C_{1-6}$ alkyl group, a $C_{1-6}$ alkyl group substituted by at least one hydroxy, $C_{1-6}$ alkoxy group, $C_{1-6}$ alkanoyloxy, phenyl, amino, $C_{1-6}$ alkylamino, di $C_{1-6}$ alkylamino, diphenyl $C_{1-6}$ alkylamino or N,$C_{1-6}$ alkyl, N-phenyl $C_{1-6}$ alkylamino group; or a pharmaceutically acceptable salt of a compound of formula I or II.

2. The compound of claim 1 wherein $R_2$ is piperidino, morpholino or N-methyl-piperazinyl.

3. A compound as claimed in claim 1 which is 1-ethyl-1,4-dihydro-7-(4-methyl-1-piperazinyl)-4-oxo-N(1H-tetrazol-5-yl)-1,8-naphthyridine-3-carboxamide.

4. A compound as claimed in claim 1 which is 1-ethyl-1,4-dihydro-7-morpholino-4-oxo-N(1H-tetrazol-5-yl)-1,8-naphthyridine-3-carboxamide.

5. A compound as claimed in claim 1 which is 1-ethyl-1,4-dihydro-4-oxo-7-piperidine-N(1H-tetrazol-5-yl)-1,8-naphthyridine-5-carboxamide.

6. A pharmaceutical composition for treating conditions due to a combination of an antigen with a reaginic antibody in which the condition is extrinsic asthma, hay fever, urticaria, exzema or atopic dermatitis comprising an effective amount of a compound as claimed in claim 1 if desired in the form of a pharmaceutically acceptable salt together with an inert pharmaceutical carrier or diluent.

7. A method of treating a patient suffering from or liable to a condition resulting primarily from the combination of an antigen with a reaginic antibody in which the condition is extrinsic asthma, hay fever, urticaria, exzema or atopic dermatitis which comprises administering to said patient by oral ingestion or inhalation an effective amount of a compound as claimed in claim 1, if desired in the form of a pharmaceutically acceptable salt to alleviate said condition.

* * * * *